(12) United States Patent
Cortial et al.

(10) Patent No.: US 10,266,553 B2
(45) Date of Patent: Apr. 23, 2019

(54) TRANSFER AGENT FOR THE PREPARATION OF A FUNCTIONAL OR TELECHELIC POLYOLEFIN

(71) Applicants: COMPAGNIE GENERALE DES ETABLISSEMENTS MICHELIN, Clermont-Ferrand (FR); MICHELIN RECHERCHE ET TECHNIQUE, S.A., Granges-Paccot (CH); UNIVERSITE CLAUDE BERNARD LYON 1, Villeurbanne (FR); CENTRE NATIONAL DE LA RECHERCE SCIENTIFIQUE, Paris (FR); CPE LYON FORMATION CONTINUE ET RECHERCHE, Villeurbanne (FR)

(72) Inventors: Guillaume Cortial, Clermont-Ferrand (FR); Julien Thuilliez, Clermont-Ferrand (FR); Christophe Boisson, Tramoyes (FR); Franck D'Agosto, Genas (FR); Sébastien Norsic, Lyons (FR)

(73) Assignees: COMPAGNIE GENERALE DES ETABLISSEMENTS MICHELIN, Clermont-Ferrand (FR); MICHELIN RECHERCHE ET TECHNIQUE S.A., Granges-Paccot (CH); UNIVERSITE CLAUDE BERNARD LYON 1, Villeurbanne (FR); CENTRE NATIONAL DE LA RECHERCHE SCIENTIFIQUE, Paris (FR); CPE LYON FORMATION CONTINUE ET RECHERCHE, Villeurbanne (FR)

( * ) Notice: Subject to any disclaimer, the term of this patent is extended or adjusted under 35 U.S.C. 154(b) by 0 days.

(21) Appl. No.: 15/528,688

(22) PCT Filed: Dec. 11, 2015

(86) PCT No.: PCT/FR2015/053458
§ 371 (c)(1),
(2) Date: May 22, 2017

(87) PCT Pub. No.: WO2016/092237
PCT Pub. Date: Jun. 16, 2016

(65) Prior Publication Data
US 2017/0253619 A1    Sep. 7, 2017

(30) Foreign Application Priority Data
Dec. 12, 2014 (FR) .................................. 14 62328

(51) Int. Cl.
*C07F 7/08* (2006.01)
*C08F 10/02* (2006.01)

(52) U.S. Cl.
CPC ............ *C07F 7/0816* (2013.01); *C07F 7/081* (2013.01); *C08F 10/02* (2013.01)

(58) Field of Classification Search
None
See application file for complete search history.

(56) References Cited

U.S. PATENT DOCUMENTS

| 2007/0010639 A1 | 1/2007 | Makio et al. |
| 2013/0274407 A1 | 10/2013 | Cortial et al. |
| 2014/0220733 A1* | 8/2014 | Hunks ............... C07C 251/08 438/102 |

FOREIGN PATENT DOCUMENTS

| WO | 2007054224 A2 | 5/2007 |
| WO | 2010139450 A1 | 12/2010 |
| WO | 2013135314 A1 | 9/2013 |

OTHER PUBLICATIONS

Shiono et al., Macromolecules (1994), 27(9), 2635-7. (Year: 1994).*
Felix et al. Main Group Chemistry, 2012, 11(1), 13-29. (Year: 2012).*
International Search Report and Written Opinion regarding PCT/FR2015/053458 dated Feb. 10, 2016.
Felix, Ana M. et al: Insertion of CO2 into divalent group 2 and 12 bis(silylamides).
Cornelia Schmaunz et al: Inter- and Intramolecular [4_2]-Cycloaddition Reactions with 4, 4-Disubstitute, N-Silyl-1, 4-dihydropyridines as Precursors for N-Protonated 2-Azabutadiene Intermediates, vol. 46, No. 12, Apr. 1, 2014 (Apr. 1, 2014), pp. 1630-1638.
Kei Murakami et al: Cobalt-Catalyzed Benzylzincation of Alkynes, Chemistry—A European Journal, vol. 16, No. 26, Jul. 12, 2010 (Jul. 12, 2010), pp. 7688-7691.
Basha F Z et al: A Novel Three Carbon-Amino Grignard Reagent—Its Use in an Efficient Pyrrolidine Synthesis, Tetrahedron Letters, Pergamon, GB, vol. 25, No. 46, Jan. 1, 1984 (Jan. 1, 1984), pp. 5271-5274.
Langer F et al: Preparation of polyfunctional phosphines using zinc organometallics, Tetrahedron Asymmetry, Pergamon Press Ltd., Oxford, GB, vol. 8, No. 5, Mar. 13, 1997 (Mar. 13, 1997), pp. 715-738.

(Continued)

*Primary Examiner* — Clinton A Brooks
*Assistant Examiner* — Kofi Adzamli
(74) *Attorney, Agent, or Firm* — Dickinson Wright PLLC

(57) ABSTRACT

A compound and the use thereof to prepare a functional or telechelic polyolefin is provided. The compound has the following formula (II):

$$Y((CH_2)_p\text{—}B')_m \qquad \text{(II), wherein}$$

m=2 or 3;
Y being an alkaline earth metal or zinc when m=2,
Y being aluminum when m=3;
B' being selected from the group comprising $N(SiMe_3)_2$; $N(SiMe_2CH_2CH_2SiMe_2)$; $C_6F_5$; $C_3F_7$; $C_6F_{13}$; para-$C_6H_4$—$NMe_2$; para-$C_6H_4$—O-Me; para-$C_6H_4$—$N(SiMe_3)_2$; and $CH(OCH_2CH_2O)$; and
p being an integer from 0 to 50.

10 Claims, No Drawings

(56) References Cited

OTHER PUBLICATIONS

Database Reaxys [Online] Elsevier; 1989, Larcheveque et al: XRN 5505121, XP002753781, Database accession No. XRN 5505121 abrégé & Larcheveque et al: Bull. Chem. Soc. Chim. Fr., 1989, pp. 130-139.

Database Reaxys [Online] Elsevier; 2007, Allef et al: XRN 15774419, XP002753782, Database accession No. XRN 15774419 abrégé & Allef et al: Heterocycles, vol. 74, 2007, pp. 421-436.

Angewandte Chemie International Edition, Telechelic Polyethylene from Catalyzed Chain-Growth Polymerization, Dr. Ian German, et al., Feb. 13, 2013.

Intech, End-capped Oligomers of Ethylene, Olefins and Dienes, by means of Coordinative Chain Transfer Polymerization using Rare Earth Catalysts, Thomas Chenal and Marc Visseaux.

Macromolecules 1995, 28, 7256-7261, Degradable Cyclooctadiene/ Acetal Copolymers: Versatile Precursors to 1,4-Hydroxytelechelic Polybutadiene and Hydroxytelechelic Polyethylene, Cassandra Fraser, et al.

Chem. Rev. 2003, 103, 283-315, Advances in Non-Metallocene Olefin Polymerization Catalysis, Vernon C. Gibson, et al.

Angewandte Chemie International Edition, Polyethylene Building Blocks by Catalyzed Chain Growth and Efficient End Functionalization Strategies, Including Click Chemistry, Rémi Briquel, et al; Oct. 29, 2008.

Macromolecules 2010, 43 7495-7503, Thiol-End-Functionalized Polyethylenes, Jérôme Mazzolin, et al., received Jun. 7, 2010.

Chem Commun (Camb). Jul. 7, 2011;47(25): 7057-9. doi: 10.1039/c1cc12620b. Epub May 31, 2011, Polyethylenes bearing a terminal porphyrin group, Unterlass MM, et al.

Macromolecules 2011, 44, 3381-3387, Polyethylene End Functionalization Using Radical-Mediated Thiol-Ene Chemistry: Use of Polyethylenes Containing Alkene End Functionality, Jerome Mazzolini, e tal.

Macromol Rapid Commun. Sep. 15, 2011; 32(18):1447-53. doi: 10.1002/march.201100310. Epub Jul. 13, 2011, Synthesis of cyclopentadienyl capped polyethylene and subsequent block copolymer formation via hetero Diels-Alder (HDA) chemistry, E. Espinosa, et al.

Aggew. Chim. In. Ed. 2013, 52, 3438-3441, Telechelic Polyethylene from Catalyzed Chain-Growth Polymerization, Ian German, et al.

* cited by examiner

TRANSFER AGENT FOR THE PREPARATION OF A FUNCTIONAL OR TELECHELIC POLYOLEFIN

CROSS REFERENCE TO RELATED APPLICATIONS

This application is a 371 national phase entry of PCT/FR2015/053458, filed 11 Dec. 2015, which claims benefit of French Patent Application No. 1462328, filed 12 Dec. 2014, the entire contents of which are incorporated herein by reference for all purposes.

FIELD OF THE INVENTION

The present invention relates to compounds referred to as functional transfer agents, and the catalytic systems comprising these functional transfer agents. These transfer agents may be used in a method for synthesizing functional or telechelic polyolefins, but also functional or telechelic polyolefins one (or each) end of the main polymer chain of which has been functionalized. These polyolefins may be used as matrix/base structure in organic, inorganic, hybrid or composite materials.

RELATED ART

Generally, a polymer which may give rise to a new polymerization or a new reaction is referred to as a "functional polymer" in light of the reactivity of one of its chain ends, or "telechelic polymer" in light of the reactivity of each of its chain ends. In this type of molecule, the reactive groups situated at the chain ends do not originate from monomers.

Several methodologies for synthesizing functional polyolefins based on ethylene have been described in the prior art.

A first method consists in polymerizing the ethylene (and/or a mono-alpha-olefin) in the presence of a two-component catalytic system based on a transfer agent. This type of method makes it possible especially to obtain a polyolefin with a vinyl end group (Boisson, D'Agosto et al., Angew Chem Int Ed Engl. 2013, 52, 3438-3441). This vinyl end group may be chemically modified by means of additional steps (T. Chenal and M. Visseaux, "End-capped Oligomers of Ethylene, Olefins and Dienes, by means of Coordinative Chain Transfer Polymerization using Rare Earth Catalysts", INTECH, 2014, 4—Oligomerization of chemical and biological compounds, chapter 1, pages 3-30).

A second method consists in chemically modifying the polyolefin, in bulk or in solution. These are generally radical-type reactions, which make it possible to introduce functionality along the main polymer chain. However, this method has at least the two following drawbacks:
  the formation of branched architectures which may adversely affect the properties of the polyolefin,
  the random introduction of functional groups, rather than in a controlled manner at the end of the main polymer chain.
A third method consists in:
  polymerizing a diene monomer in a controlled manner via the anionic route,
  functionalizing this polymer by a functional termination agent,
  hydrogenating this polymer so as to obtain a functional polyolefin.

This third method has the drawback of requiring a succession of steps and the use of different types of solvents, which may make it complex and expensive.

Several routes for synthesizing telechelic polymers have been described in the prior art. Nonetheless, in terms of synthesizing telechelic polyolefins, three main methods have been developed:

(i) the first relates to the synthesis of a hydroxy telechelic polybutadiene via the anionic route. The butadiene is firstly polymerized before a step of hydrogenation of the unsaturations of the polymer chain. The telechelic polyethylene obtained in this way has identical chain ends; it is also branched in light of the presence of the ethyl groups resulting from the 1,2-units of the butadiene. This type of polymer is commercially available under the name Kraton L2203.

(ii) another synthesis pathway relates to cyclooctadiene ring-opening methathesis polymerization. The polymer obtained is then hydrogenated to give a hydroxy telechelic polyolefin (Hillmyer et al., Macromolecules 1995, 28, 7256-7261).

(iii) finally, the living polymerization of ethylene in the presence of a palladium-based complex has also been discussed. This complex makes it possible not only to initiate the living polymerization reaction of the ethylene, but also to functionalize the chain ends. The branched telechelic polyethylene obtained has either identical ester functions or one ester function and one ketone function at the chain ends (Brookhart, Macromolecules 2003, 36, 3085). In the same vein, the document US 2007/0010639 describes the three-step synthesis of telechelic polypropylene having polar chain ends. Olefinic monomers bearing protected functional groups are used at the start of polymerization to create a short segment bearing these functions laterally. (Co)polymerization of propylene is then undertaken. A functional monomer is then used once again to form a second short terminal segment bearing functions laterally.

The term "living polymerization" is intended to mean a chain-growth polymerization which does not comprise chain termination or transfer reactions. Living polymerizations of olefins make it possible to prepare polymers which are functional at one or at both chain ends. However, within the field of olefin polymerization, living polymerizations are limited by the fact that only a single chain is produced per transition metal, which poses a problem in terms of production costs. Polymerization by coordination catalysis has the advantage of producing a large number of chains per transition metal. There is therefore a need for a system which makes it possible to prepare telechelic polyolefins, especially of polyethylene, under conditions of polymerization by coordination catalysis which are satisfactory in terms of production costs.

Document WO2013/135314 describes a telechelic polyolefin, at least one end of the polymer chain of which is necessarily a vinyl group, which may optionally be functionalized. This polyolefin is obtained by polymerization of ethylene in the presence of a transfer agent comprising a vinyl function. The method described in this prior art relates more particularly to a polyolefin obtained by polymerization of at least 95 mol % of ethylene, in the presence of a transfer agent of di(alkenyl)magnesium type preferably containing 6 to 9 $CH_2$ groups between the magnesium and the vinyl function.

As regards the compounds of the prior art designated as functional transfer agents, they have certain limitations.

By way of example, WO2013/135314 describes functional transfer agents of the $Mg((CH_2)_9-CH=CH_2)_2$ type, which may be used to prepare telechelic polyolefins. The latter have the drawback of providing a vinyl functional group CH=CH$_2$ at one chain end, which function is devoid of heteroatoms, which may constitute a limitation in certain applications.

Document US 2013/0274407 describes functional transfer agents corresponding to the formula (AT) below. These compounds make it possible to introduce, at one end of the polybutadiene chain, aromatic groups bearing heteroatoms. However, the presence of an aromatic ring may be limiting depending on the envisaged application.

(AT)

The problem that embodiments of the present invention aims to solve relates especially to the synthesis of a polyolefin, one or both of the ends of the main chain of which is/are functionalized and modifiable. This polyolefin may especially be a homopolyethylene or a copolymer obtained by copolymerization of ethylene with an α-monoolefin.

SUMMARY

The Applicants have developed a transfer agent which enables the preparation of a polyolefin, at least one, and advantageously both, of the chain ends of which each has (have) a functional group. In other words, this is a transfer agent which enables the preparation of a polyolefin, at least one of the ends of which may readily react in order to facilitate the incorporation of said polyolefin in, for example, a hydrophilic or hydrophobic environment, in organic, inorganic, hybrid or composite materials.

This polyolefin is advantageously telechelic (functionalization of both ends) and linear. It advantageously has two distinct chain ends, which may react selectively in light of their difference in reactivity.

The Applicants have developed compounds designated as functional transfer agent, and the method for preparation thereof.

The polyolefin, the synthesis of which is made possible by the use of the transfer agent in accordance with embodiments of the invention, bears at least one chain end function, derived from the compound designated as functional transfer agent, corresponding to formula (II).

More precisely, the method for preparing a polyolefin having at least one functionalized chain end comprises the following step (a):

(a) preparation of a compound of formula (I), by homopolymerization of ethylene or by copolymerization of ethylene and of an alpha-monoolefin in the presence of a transfer agent of formula (II):

Y-(A-(CH$_2$)$_p$—B')$_m$ (I)

Y((CH$_2$)$_p$B')$_m$ (II)

in which:
  when m=2, Y is an alkaline earth metal or zinc, and
  when m=3, Y is aluminium;

A is a polymer chain obtained by polymerization of ethylene or by copolymerization of ethylene and of an alpha-monoolefin;

B' is selected from the group comprising N(SiMe$_3$)$_2$; N(SiMe$_2$CH$_2$CH$_2$SiMe$_2$); para-C$_6$H$_4$(NMe$_2$); para-C$_6$H$_4$(OMe); C$_6$H$_4$(N(SiMe$_3$)$_2$); C$_6$F$_5$; C$_3$F$_7$; C$_6$F$_{13}$; and CH(OCH$_2$CH$_2$O);

p is an integer from 0 to 50, advantageously from 0 to 11.

DETAILED DESCRIPTION

In the present application, "an" alpha-monoolefin is intended to mean one or more alpha-monoolefins, preferably a single alpha-monoolefin.

The abovementioned compounds N(SiMe$_3$)$_2$; N(SiMe$_2$CH$_2$CH$_2$SiMe$_2$); C$_6$F$_5$; C$_3$F$_7$; C$_6$F$_{13}$; para-C$_6$H$_4$—NMe$_2$; para-C$_6$H$_4$—O-Me; para-C$_6$H$_4$—N(SiMe$_3$)$_2$; and CH(OCH$_2$CH$_2$O) correspond respectively to the following compounds (* denotes a carbon atom devoid of hydrogen and ** denotes a CH group):

Generally, the group B' resulting from the transfer agent is not a vinyl group.

Advantageously, the polymer chain A is a linear polyethylene or a copolymer obtained by copolymerization of ethylene and of an alpha-monoolefin (a single polymerizable carbon=carbon double bond). Alpha-monoolefin is intended also to mean styrene and any other monomer of vinylaromatic type.

The alpha-monoolefin used in embodiments of the invention is advantageously selected from the group comprising olefins of formula CH$_2$=CH—C$_x$H$_{2x+1}$ (x=1 to 6), styrene, and styrene derivatives.

Advantageously, the polymer chain A is a polymer of:
  70 to 100 mol % of ethylene monomer, more advantageously 95 to 99.9 mol %;
  0 to 30 mol % of an alpha-monoolefin selected from the group comprising alpha-monoolefins, styrene and any other monomer of vinylaromatic type, more advantageously 0.1 to 5 mol %; advantageously, when the alpha-monoolefin is selected from the group comprising olefins of formula CH$_2$=CH—C$_x$H$_{2x+1}$ (x=1 to 6), styrene and styrene derivatives.

According to a preferred embodiment, the polymer chain A is a linear polyethylene, that is to say an ethylene homopolymer of formula —(CH$_2$—CH$_2$)$_n$—, n being an integer advantageously from 7 to 3600, even more advantageously from 17 to 360.

The polymer chain A advantageously has a number-average molar mass of between 200 g/mol and 100 000 g/mol, more advantageously between 500 g/mol and 50 000 g/mol, more advantageously between 500 g/mol and 20 000 g/mol, and even more advantageously between 500 g/mol and 10 000 g/mol.

The number-average molar mass may especially be obtained by size exclusion chromatography according to the general knowledge of those skilled in the art. By way of indication, those skilled in the art may refer to the protocol described in the document WO 2010/139450.

The transfer agent of formula (II) which may be in a method for preparing a polyolefin of formula (I), (III) or (IV), is part of embodiments of the present invention:

$$Z\text{-}A\text{-}(CH_2)_p\text{—}B' \qquad (III)$$

$$Z\text{-}A\text{-}(CH_2)_p\text{—}B \qquad (IV)$$

As already indicated, the transfer agent of formula (II) $Y((CH_2)_p\text{—}B')_m$ is advantageously defined by:

m=2 or 3;

Y is an alkaline earth metal or zinc when m=2;

Y is aluminium when m=3;

B' is selected from the group comprising $N(SiMe_3)_2$; $N(SiMe_2CH_2CH_2SiMe_2)$; $C_6F_5$; $C_3F_7$; $C_6F_{13}$; para-$C_6H_4$—$NMe_2$; para-$C_6H_4$—O-Me; para-$C_6H_4$—N$(SiMe_3)_2$; and $CH(OCH_2CH_2O)$;

p is an integer from 0 to 50, advantageously from 0 to 11.

According to a particular embodiment, the integer p is at least equal to 1. It may thus be from 1 to 50 or from 1 to 11.

The polyolefins of formulae (I), (III) and (IV) are advantageously linear. The polyolefins of formulae (III) and (IV) advantageously have two distinct chain ends, which may react selectively in light of their difference in reactivity.

By way of example, the method for synthesizing the transfer agent of formula (II) advantageously comprises the reaction of the metal (especially when m=2 and Y=Mg) with a compound of formula X—$(CH_2)_p$—B', X being a halogen, preferably a bromine atom, B' being chosen from the group comprising $N(SiMe_3)_2$; $N(SiMe_2CH_2CH_2SiMe_2)$; $C_6F_5$; $C_3F_7$; $C_6F_{13}$; para-$C_6H_4$—$NMe_2$; para-$C_6H_4$—O-Me; para-$C_6H_4$—$N(SiMe_3)_2$; and $CH(OCH_2CH_2O)$; and p being an integer from 0 to 50.

On the other hand, when Y=Al, the transfer agent is advantageously prepared from $AlCl_3$.

According to a preferred embodiment, the group B' of the transfer agent of formula (II) is advantageously $N(SiMe_2CH_2CH_2SiMe_2)$ or $N(SiMe_3)_2$.

The transfer agent is advantageously a magnesium compound.

According to a particular embodiment, it is $Mg[(CH_2)_p\text{—}N(SiMe_2CH_2CH_2SiMe_2)]_2$ or $Mg[(CH_2)_p\text{—}N(SiMe_3)_2]_2$, with p=1 to 11, and preferentially p=3.

The polyolefin of formula (I) is advantageously obtained in a multi-component catalytic system comprising the transfer agent of formula (II) and a catalyst. This catalyst corresponds to a compound making it possible to generate an active species for catalysing the formation of the polymer chain A. This may especially be a catalyst based on a transition metal or on a lanthanide, advantageously a metallocene comprising the base structure $(Cp^1)(Cp^2)M$ or $E(Cp^1)(Cp^2)M$.

This catalyst makes it possible to carry out catalytic polymerization of the olefin (ethylene and where appropriate alpha-monoolefin) by coordination/insertion, with a large number of polymer chains being produced per catalyst molecule.

M is generally a group 3 or 4 metal, or a lanthanide.

In addition, $Cp^1$ is advantageously a cyclopentadienyl, fluorenyl or indenyl group, this group being substituted or unsubstituted.

$Cp^2$ is advantageously a cyclopentadienyl, fluorenyl or indenyl group, this group being substituted or unsubstituted.

The group E is a group bridging the ligands $Cp^1$ and $Cp^2$. The metallocenes with which the two groups $Cp^1$ and $Cp^2$ are bridged are commonly referred to as ansa-metallocenes. The group E may especially be of formula $M'R^1R^2$ in which M' is a group 14 element or a chain of group 14 elements; $R^1$ and $R^2$ being identical or different and selected from the group comprising alkyl or aryl groups comprising from 1 to 20 carbon atoms. The group E may for example be —$C(CH_3)_2$—, —$CH_2$—$CH_2$—, or —$Si(CH_3)_2$—.

The compound based on a transition metal or a lanthanide may also have a non-metallocene structure, such as those defined in the review by V. C. Gibson and S. K. Spitzmesser (*Chem. Rev.* 2003, 103, 283-315).

Where appropriate, especially when the metal of the compound is not a lanthanide or a group 3 metal, a cocatalyst may be used in combination with the catalyst described above. Those skilled in the art will know how to choose the appropriate cocatalyst.

According to a particularly preferred embodiment, the catalyst may be obtained from the metallocene compound of formula $(C_5Me_5)_2MX_2Li(OEt_2)_2$, M being a group 3 metal or a lanthanide, and X preferentially being a halogen. This may advantageously be a compound of a lanthanide, preferably Nd, and especially $(C_5Me_5)_2NdCl_2Li(OEt_2)_2$.

The catalyst may also be obtained from a lanthanide metallocene compound such as, for example, the compounds $\{(Me_2Si(C_{13}H_8)_2)Nd(\mu\text{-}BH_4)[(\mu\text{-}BH_4)Li(THF)]\}_2$, $Me_2Si(C_{13}H_8)_2Nd(BH_4)(THF)$, $(Me_2Si(2,7\text{-}tBu_2\text{-}C_{13}H_6)_2)Nd(BH_4)(\mu\text{-}BH_4)Li(ether)_3$, $Me_2Si(3\text{-}Me_3Si\text{—}C_5H_3)_2NdBH_4(THF)_2$; $\{Me_2Si(3\text{-}Me_3Si\text{—}C_5H_3)_2NdCl\}$; $\{Me_2Si(C_5H_4)(C_{13}H_8)NdCl\}$; and $[Me_2Si(C_5H_4)(C_{13}H_8)Nd(BH_4)_2][Li(THF)]$.

The catalyst may especially be obtained from a borohydride metallocene compound of a lanthanide, such as described in the document WO 2007/054224.

Derivatives of the monofunctional polyolefin of formula (I), that is to say any polyolefin resulting from the termination, for example by hydrolysis, of at least one of the chain ends of the polyolefin of formula (I) and from the modification of the group B' according to reactions known to those skilled in the art, may also be prepared according to embodiments of the present invention.

Thus, in the method for preparing the polyolefin having at least one functionalized chain end, step (a) is advantageously followed by a step (b) which consists in reacting the compound of formula (I) with a chain termination agent.

This termination agent may advantageously be a functionalization agent.

It enables the cleavage of the Y-A bonds of the polyolefin of formula (I).

According to a particular embodiment, step (b) may be followed by a step (c) which is a reaction for modification of the function B', preferably a deprotection reaction, to give a function B.

The step (b) may especially be a step of functionalization by Z, which may be carried out:

by successive addition of $B(OR)_3$ and of $NMe_3O$, R being a $C_1$-$C_4$ alkyl; or by addition of a functionalization agent, especially being able to be selected from the group comprising iodine, sulphur, oxygen, nitroxyl radicals; carbon dioxide; chlorosilanes such as $ClSiR_2H$ or $Cl_2SiRH$ (R being an alkyl group having from 1 to 20 carbons); isobutene; alkoxysilanes such as $SiMe_2(OMe)_2$, $SiX(OMe)_3$, $SiXMe(OMe)_2$ ($X=(CH_2)_nY$, with n=1 to 20 and $Y=OMe$, $NMe_2$, $S(SiMe_2(CMe_3))$, $N(SiMe_3)_2$; alkyl halides; aryl halides; vinyl halides; and disulphides such as $CS_2$ or tetraethylthiuram disulphide.

The step of functionalization by Z is advantageously carried out by addition of iodine, or sulphur, or tetraethylthiuram disulphide or O,O-diethyl dithiobis[thioformate].

This second step of the method actually consists of introducing the Z group by cleaving the Y-A bonds of the compound of formula (I).

One of the advantages of the method for preparing the polyolefin consists in being able to carry out all the steps (a-b or a-c) in situ. Indeed, unlike the methods of the prior art relating to the preparation of monofunctional or telechelic polyolefins, the method described above makes it possible to dispense with the steps of separation/isolation/purification of the intermediate compounds by virtue of the fact that the second step can be carried out in situ. The polymerization and the functionalization may advantageously be carried out successively, without intermediate purification step, and especially in the same reactor.

In addition, the polymerization has a pseudo-living nature, this method makes it possible to control the molar mass to obtain a relatively narrow distribution of molar masses, advantageously less than 1.5.

The experimental conditions generally make it possible to control the molar mass of the polyolefin of formula (III) or (IV) but also its degree of functionalization of the ends by B' (or B) and Z groups. The degree of functionalization may be estimated by % F:

% F=100×[number of B' (or B) ends per chain]×[number of Z ends per chain], the maximum number of B' (or B) ends per chain being fixed at most at 1.

The numbers of B' (or B) and Z ends are determined by NMR (nuclear magnetic resonance) according to techniques known to those skilled in the art.

The degree of functionalization may thus advantageously be greater than 70%, and even more advantageously greater than 90%. In other words, the method of embodiments of the invention makes it possible to advantageously produce at least 90% of monofunctional or telechelic polyolefins.

Advantageously, the step (b) makes it possible to obtain a polyolefin of formula (III) or (IV)

  (III)

  (IV)

in which:
A is a polymer chain obtained by homopolymerization of ethylene or by copolymerization of ethylene and of an alpha-monoolefin;
B' is selected from the group comprising $N(SiMe_3)_2$; $N(SiMe_2CH_2CH_2SiMe_2)$; para-$C_6H_4(NMe_2)$; para-$C_6H_4(OMe)$; $C_6H_4(N(SiMe_3)_2)$; $C_6F_5$; $C_3F_7$; $C_6F_{13}$; $CH(OCH_2CH_2O)$;
B is the function B' or a function deriving from B';
p is an integer from 0 to 50, advantageously from 0 to 11;
Z is a function selected from the group consisting of the hydrogen atom; halogens; thiols; thiol derivatives; azides; amines; alcohols; carboxylic acid function; isocyanates; silanes; phosphorus-based derivatives; dithioesters, dithiocarbamates; dithiocarbonates; trithiocarbonates; alkoxyamines; vinyl function; dienes; and the group -A-$(CH_2)_p$—B'.

When Z=H, the polyolefin of formula (III) or (IV) is advantageously obtained by cleavage of the Y-A bonds by hydrolysis, preferentially with a protic constituent such as methanol.

When Z≠H, the polyolefin of formula (III) or (IV) is telechelic. In this case, the groups A, B', B are as described above, while Z is a function selected from the group consisting of: halogens; thiols; thiol derivatives; azides; amines; alcohols; carboxylic acid function; isocyanates; silanes; phosphorus-based derivatives; dithioesters, dithiocarbamates; dithiocarbonates; trithiocarbonates; alkoxyamines; vinyl function; dienes; and the group -A-$(CH_2)_p$—B'.

The present invention also enables the preparation of derivatives of the telechelic (Z≠H) polyolefin of formula (III) or (IV), that is to say any polyolefin resulting from the functionalization of at least one of the chain ends of the telechelic polyolefin of formula (III) or (IV). This therefore concerns the modification of the group B' and/or the group Z, according to reactions known to those skilled in the art.

Modification of the group B' to give a group B makes it possible to obtain a polyolefin of formula (IV) Z-A-$(CH_2)_p$—B, in which B denotes a function derived from the function B'. The function B generally denotes either the function B' or a function derived from B', that is to say a function obtained by modification of B according to reactions known to those skilled in the art. The function B may especially be $NH_2$, $NH_3^+X^-$ (with X=halogen, for example).

According to a particularly preferred embodiment, the group Z in the formulae (III) and (IV) is a halogen—even more advantageously an iodine atom, I—or a dithiocarbamate such as diethyldithiocarbamate (S—C(=S)—N(Et)$_2$) or a dithiocarbonate such as S—C(=S)—OEt.

The ends of the main polymer chain of the telechelic polyolefin of formula (III) or (IV) may have two groups, in this instance B' (or B) and Z, the respective reactivities of which are very different from one another, the Z function advantageously being distinct from the B' (or B) function.

Consequently, and according to a particularly preferred embodiment, the telechelic polyolefin is of formula (IV) B—$(CH_2)_p$-A-Z, Z preferentially being an iodine atom or a dithiocarbamate, p being an integer from 0 to 11, B preferentially being the group $NH_3Cl$. Advantageously, the polymer chain A is the polyethylene $(CH_2—CH_2)_n$, n being an integer from 7 to 3600, advantageously from 17 to 360.

According to a particular embodiment, the telechelic polyolefin is of formula (IV) and is obtained when:
A is polyethylene;
A has an average molar mass of between 500 and 100 000 g/mol;
B=$ClH_3N$;
p=1 to 11;
Y=Mg;
Z=I;
the compound of formula (I) is prepared in the presence of the catalyst employing the compound $(C_5Me_5)_2NdCl_2Li(OEt_2)_2$.

It may advantageously be obtained according to the method which consists in:
preparing the compound of formula (I) (with A=$(CH_2—CH_2)_n$, B'=$(CH_2)_p$—$N(SiMe_2CH_2CH_2SiMe_2)$; p=3; n=16 to 360) by polymerization of ethylene, $CH_2=CH_2$, in the presence of $(C_5Me_5)_2NdX_2$ Li(OEt$_2$)$_2$, X being a halogen, and of transfer agent Mg((CH$_2$)$_3$—N(SiMe$_2$CH$_2$CH$_2$SiMe$_2$))$_2$;

functionalizing by Z, by addition of I$_2$ and modification of the group B' to give the group B=ClH$_3$N so as to obtain the telechelic polyolefin ClH$_3$N—(CH$_2$)$_3$—(CH$_2$—CH$_2$)$_n$—I.

In relation to derivatives of the monofunctional or telechelic polyolefin of formula (III) or (IV), they may, as already mentioned, be obtained by the method described above, especially by modification of at least one of the ends of the telechelic polyolefin, preferably the function B' (or B), in a step subsequent to the functionalization by Z.

Indeed, in light of the groups B' (or B) and Z of the telechelic polyolefin of formula (III) or (IV), the two groups may be easily modified subsequently by organic chemistry, to introduce new groups either via the group Z or via the group B' (or B) as has been detailed for example with monofunctional polyethylenes by D'Agosto, Boisson et al. (R. Briquel, J. Mazzolini, T. Le Bris, O. Boyron, F. Boisson, F. Delolme, F. D'Agosto, C. Boisson, R. Spitz, *Angew. Chem. Int. Eng. Ed.*, 47, 9311-9313 (2008); J. Mazzolini, R. Briquel, I. Mokthari, O. Boyron, V. Monteil, F. Delolme, D. Gigmes, D. Bertin, F. D'Agosto, C. Boisson, *Macromolecules* 43, 7495-7503 (2010); M. Unterlass, E. Espinosa, F. Boisson, F. D'Agosto, C. Boisson, K. Ariga, I. Khalakhan, R. Charvet, J P. Hill, *Chem. Commun.* 47, 7057-7059 (2011); Mazzolini, O. Boyron, V. Monteil, D. Gigmes, D. Bertin, F. D'Agosto, C. Boisson, *Macromolecules* 44, 3381-3387 (2011); E. Espinosa, M. Glassner, C. Boisson, C. Barner Kowollik, F. D'Agosto, *Macromol. Rapid Commun.* 32, 1447-1453 (2011); I. German, W. Khelifi, S. Norsic, C. Boisson, F. D'Agosto, *Angew. Chem. Int. Engl. Ed.*, 52, 3438-3441(2013)).

Thus, the telechelic polyolefin of formula (III), B'—(CH$_2$)$_p$-A-Z (or (IV) B—(CH$_2$)$_p$-A-Z), may be subsequently modified.

The (telechelic or non-telechelic) polyolefins (III) or (IV) and their derivatives may be used as additive for the modification of organic, inorganic, hybrid or composite materials, or as reactive synthon for polymerization.

The fields of interest of the present invention especially relate, non-limitingly, to additives for polyolefins, modifiers of organic and inorganic fillers, cosmetics, adhesives, inks, waxes, lubricants or coatings.

The telechelic or non-telechelic (Z=H) polyolefins and their derivatives may be used in the context of preparation of original materials or architectures, based especially on polyethylene and polypropylene.

Unlike the methods of the prior art, embodiments of the present invention make it possible to obtain, in a single step, a (telechelic or non-telechelic) polyolefin comprising a chain end of ammonium, amine, acetal, aldehyde, fluoroalkyl ether or perfluoroaryl type. It is the nature of the transfer agent, and especially its group B', which enables this direct, and rapid, functionalization. The presence of an ammonium function at the chain end is particularly attractive with the aim of facilitating its incorporation into more complex organic or inorganic structures.

The invention and the resultant advantages thereof will become clearer from the following illustrative and non-limiting examples

EXEMPLARY EMBODIMENTS

Polyethylenes of formula (IV) were prepared from the transfer agent MgR$_2$ (R=(CH$_2$)$_3$—N(SiMe$_2$CH$_2$CH$_2$SiMe$_2$) or (CH$_2$)$_3$—N(SiMe$_3$)$_2$) described below.

Nuclear Magnetic Resonance (NMR).

High-resolution NMR spectroscopy was carried out on a Bruker DRX 400 spectrometer operating at 400 MHz for protons. The acquisitions were carried out at 363 K using a 5 mm QNP probe. The samples were analysed at a concentration of 5-15% by weight. A mixture of tetrachloroethylene (TCE) and deuterated benzene (C$_6$D$_6$) (2/1 v/v) was used as solvent. Chemical shifts are given in ppm units relative to tetramethylsilane as internal reference.

Size Exclusion Chromatography (SEC).

High-temperature size exclusion chromatography (HT-SEC) analyses were carried out using a Viscotek apparatus (Malvern Instruments) fitted with 3 columns (PLgel Olexis 300 mm×7 mm I. D., Agilent Technologies) and 3 detectors (refractometer, viscometer and light scattering). 200 μl of a solution of sample at a concentration of 5 mg·ml$^{-1}$ were eluted in 1,2,4-trichlorobenzene using a flow rate of 1 ml min$^{-1}$ at 150° C. The mobile phase was stabilized with 2,6-di(tert-butyl)-4-methylphenol (200 mg l$^{-1}$). The OmniSEC software was used to acquire and analyse the data. The molar masses are calculated using a calibration curve obtained from polyethylene standards (M$_p$: 170, 395, 750, 1110, 2155, 25 000, 77 500, 126 000 g·mol$^{-1}$) from Polymer Standard Service (Mainz).

Example 1

Preparation of the Transfer Agent MgR$_2$ (R=1-propyl-2,2,5,5-tetramethyl-1-aza-2,5-disilacyclopentane=(CH$_2$)$_3$—N(SiMe$_2$CH$_2$CH$_2$SiMe$_2$))

2.6 g (2 equivalents) of magnesium, then 50 ml of dry dibutyl ether are introduced into a 100 ml round-bottomed flask under an inert argon atmosphere.

The round-bottomed flask is placed in a cold bath at 0° C., and next 13.3 ml (15 g, 1 equivalent) of 1-(3-bromopropyl)-2,2,5,5-tetramethyl-1-aza-2,5-disilacyclopentane are added dropwise. The solution is left, with magnetic stirring, to gradually return to room temperature.

The solution of magnesium 1-(3-bromopropyl)-2,2,5,5-tetramethyl-1-aza-2,5-disilacyclopentane is then recovered by pipe transfer into a Schlenk flask under argon, in order to remove the unreacted magnesium.

5.5 ml (1.2 equivalents) of dioxane are added over this solution in order to shift the Schlenk equilibrium to form the compound MgR$_2$ (R=1-propyl-2,2,5,5-tetramethyl-1-aza-2,5-disilacyclopentane) and to precipitate MgBr$_2$.

This solution is then filtered over celite under argon, in order to recover MgR$_2$ in solution in dibutyl ether.

Example 2

Preparation of the Transfer Agent MgR$_2$ (R=1-propyl-2,2,5,5-tetramethyl-1-aza-2,5-disilacyclopentane=(CH$_2$)$_3$—N(SiMe$_2$CH$_2$CH$_2$SiMe$_2$))

2.6 g (2 equivalents) of magnesium, then 50 ml of dry THF are introduced into a 100 ml round-bottomed flask under an inert argon atmosphere.

Next, 13.3 ml (15 g, 1 equivalent) of 1-(3-bromopropyl)-2,2,5,5-tetramethyl-1-aza-2,5-disilacyclopentane are added dropwise at room temperature. The solution is left with magnetic stirring for one hour.

The solution of magnesium 1-(3-bromopropyl)-2,2,5,5-tetramethyl-1-aza-2,5-disilacyclopentane is then recovered by pipe transfer into a Schlenk flask under argon, in order to remove the unreacted magnesium.

5.5 ml (1.2 equivalents) of dioxane are added over this solution in order to shift the Schlenk equilibrium to form the compound $MgR_2$ (R=1-propyl-2,2,5,5-tetramethyl-1-aza-2,5-disilacyclopentane) and to precipitate $MgBr_2$.

This solution is then filtered over celite under argon, in order to recover $MgR_2$ in solution in THF.

The THF is then distilled under vacuum at room temperature and the $MgR_2$ is then dissolved in dibutyl ether.

$^1$H NMR (THF-d8—400 MHz—298 K) δ: ppm=2.63 (m, —$CH_2$—N), 1.60 (m, —$CH_2$—$CH_2$—N), 0.64 (s, N—Si$(CH_3)_2$—$CH_2$—), 0.01 (s, N—Si$(CH_3)_2$—$CH_2$—), −0.78 (Mg—$CH_2$—).

Example 3

Preparation of the Polyolefin Z-A-$(CH_2)_3$—B (with Z=H; A=$(CH_2$—$CH_2)_n$, and B=$NH_3Cl$)

21.7 ml (4.77 mmol) of $MgR_2$ prepared according to Example 2 (0.22 M in dibutyl ether) are introduced into a round-bottomed flask containing 400 ml of dry toluene.

The solution is transferred, under argon atmosphere, into a 500 ml reactor.

Next, a solution of 20.7 mg of compound $(C_5Me_5)_2NdCl_2Li.(OEt_2)_2$ (32 μmol) is transferred. The argon is then eliminated under vacuum and the reactor is pressurized to 3 bar of ethylene at 70° C. The pressure in the reactor is kept constant during the polymerization by means of a tank.

When the desired amount of ethylene has been consumed, the reactor is degassed and the temperature is brought to 20° C.

A solution of methanol/HCl is added and the medium is stirred for 1 hour.

The polymer is then filtered, washed with methanol, then dried.

15.3 g of polyethylene $CH_3$—$(CH_2CH_2)_n$—$(CH_2)_3NH_3Cl$ are recovered (functionality 82%, Mn=1850 g·mol$^{-1}$ by NMR).

$^1$H NMR (2/1 v/v TCE/$C_6D_6$, 400 MHz, 363 K) d ppm=8.29 (broad, —$NH_3Cl$), 2.87 (t, J=7 Hz, —$CH_2$—$NH_3Cl$), 1.73 (quin, J=7 Hz, —$CH_2CH_2NH_3Cl$) 1.24 (broad, $(CH_2CH_2)_n$), 0.83 (t, J=7 Hz, -$CH_2$-$CH_3$).

$^{13}$C NMR (2/1 v/v TCE/$C_6D_6$, 101 MHz, 363 K) d ppm=39.72, 32.21 30.00 ($(CH_2CH_2)_n$), 29.61, 29.25, 27.80, 26.85, 22.90, 14.04.

Example 4

Preparation of the Polyolefin Z-A-$(CH_2)_3$—B (with Z=H; A=$(CH_2$—$CH_2)_n$, and B=$NH_2$)

21.7 ml (4.77 mmol) of $MgR_2$ prepared according to Example 2 (0.22 M in dibutyl ether) are introduced into a round-bottomed flask containing 400 ml of dry toluene.

The solution is transferred, under argon atmosphere, into a 500 ml reactor.

Next, a solution of 21.4 mg of compound $(C_5Me_5)_2NdCl_2Li.(OEt_2)_2$ (33 μmol) is transferred.

The argon is then eliminated under vacuum and the reactor is pressurized to 3 bar of ethylene at 70° C. The pressure in the reactor is kept constant during the polymerization by means of a tank.

When the desired amount of ethylene has been consumed, the reactor is degassed and the temperature is brought to 20° C.

A solution of methanol/HCl is added and the medium is stirred for 1 hour.

The resulting suspension is poured into a 1 M methanol/NaOH solution and stirred for 1 hour. The polymer is then filtered, washed with methanol, then dried.

15.0 g of polyethylene $CH_3$—$(CH_2CH_2)_n$—$(CH_2)_3NH_2$ are recovered (functionality 80%, Mn=1820 g·mol$^{-1}$ by NMR).

$^1$H NMR (2/1 v/v TCE/$C_6D_6$, 400 MHz, 363 K) dppm=2.53 (broad, $CH_2$—$NH_2$), 1.24 (broad, $(CH_2CH_2)_n$), 0.83 (t, J=7 Hz, —$CH_2$—$CH_3$).

$^{13}$C NMR (2/1 v/v TCE/$C_6D_6$, 101 MHz, 363 K) d ppm=42.55, 34.44, 32.21 30.00 ($(CH_2CH_2)_n$), 29.61, 27.25, 22.90, 14.04.

Example 5

Preparation of the Telechelic Polyolefin Z-A-$(CH_2)_3$—B (with Z=I; A=$(CH_2$—$CH_2)_n$, and B=$NH_3Cl$)

8.4 ml of $MgR_2$ prepared according to Example 2 (in solution in dibutyl ether at 0.3 M) are introduced into a round-bottomed flask containing 400 ml of dry toluene.

The solution is transferred, under argon atmosphere, into a 500 ml reactor.

Next, a solution of 10.7 mg of compound $(C_5Me_5)_2NdCl_2Li.(OEt_2)_2$ (Mg/Nd mole ratio=150) is transferred.

The argon is then eliminated under vacuum and the reactor is pressurized to 3 bar of ethylene at 70° C. The pressure in the reactor is kept constant during the polymerization by means of a tank.

When the desired amount of ethylene has been consumed, the reactor is degassed and the temperature is brought to 20° C.

A solution of 2.5 g of iodine in THF (I/Mg mole ratio=4) is added and the medium is stirred for 2 hours.

A solution of methanol/HCl is added and the medium is stirred for 1 hour.

The resultant suspension is poured into methanol, then the polymer is filtered, washed in methanol, then dried.

4.5 g of telechelic polyethylene I—$(CH_2CH_2)_n$—$(CH_2)_3NH_3Cl$ are recovered (functionality 100%, Mn=1350 g·mol$^{-1}$ by NMR).

$^1$H NMR (2/1 v/v TCE/$C_6D_6$, 400 MHz, 363 K) d ppm=8.29 (broad, —$NH_3Cl$), 2.94 (t, J=7 Hz, —$CH_2I$), 2.87 (t, J=7 Hz, —$CH_2$—$NH_3Cl$), 1.73 (quin, J=7 Hz, —$CH_2CH_2NH_3Cl$), 1.66 (quin, J=7 Hz, —$CH_2CH_2I$), 1.24 (broad, $(CH_2CH_2)_n$).

$^{13}$C NMR (2/1 v/v TCE/$C_6D_6$, 101 MHz, 363 K) d ppm=39.72, 30.77, 30.00 ($(CH_2CH_2)_n$), 29.68, 29.25, 28.81, 27.80, 26.85, 4.91.

Example 6

Preparation of the Transfer Agent $MgR_2$ (R=N,N-bis(trimethylsilyl)propan-1-amine=$(CH_2)_3$—N$(SiMe_3)_2$)

2.6 g (2 equivalents) of magnesium, then 50 ml of dry THF are introduced into a 100 ml round-bottomed flask under an inert argon atmosphere.

15 g (1 equivalent) of 3-bromo-N,N-bis(trimethylsilyl)propan-1-amine are then added dropwise at room temperature. The solution is left with magnetic stirring for one hour.

The solution of magnesium 3-bromo-N,N-bis(trimethylsilyl)propan-1-amine is then recovered by pipe transfer into a Schlenk flask under argon, in order to remove the unreacted magnesium.

5.5 ml (1.2 equivalents) of dioxane are added over this solution in order to shift the Schlenk equilibrium to form the compound $MgR_2$ (R=N,N-bis(trimethylsilyl)propan-1-amine) and to precipitate $MgBr_2$.

This solution is then filtered over celite under argon, in order to recover $MgR_2$ in solution in THF.

The THF is then distilled under vacuum at room temperature and the $MgR_2$ is then dissolved in dibutyl ether to obtain a 0.40 M solution.

Example 7

Preparation of the Polyolefin Z-A-$(CH_2)_3$—B (with Z=H; A=$(CH_2—CH_2)_n$, and B=$NH_3Cl$)

6.3 ml (2.52 mmol) of $MgR_2$ prepared according to Example 6 (0.40 M in dibutyl ether) are introduced into a round-bottomed flask containing 400 ml of dry toluene.

The solution is transferred, under argon atmosphere, into a 500 ml reactor.

Next, a solution of 10.7 mg of compound $(C_5Me_5)_2NdCl_2Li.(OEt_2)_2$ (16 µmol) is transferred.

The argon is then eliminated under vacuum and the reactor is pressurized to 3 bar of ethylene at 70° C. The pressure in the reactor is kept constant during the polymerization by means of a tank.

When the desired amount of ethylene has been consumed, the reactor is degassed and the temperature is brought to 20° C.

A solution of methanol/HCl is added and the medium is stirred for 1 hour.

The polymer is then filtered, washed with methanol, then dried.

5.3 g of polyethylene $CH_3$—$(CH_2CH_2)_n$—$(CH_2)_3NH_3Cl$ are recovered (functionality 84%, Mn=1440 g·mol$^{-1}$ by NMR).

$^1$H NMR (2/1 v/v TCE/$C_6D_6$, 400 MHz, 363 K) d ppm=8.62 (broad, —$NH_3Cl$), 2.86 (—$CH_2$—$NH_3Cl$), 1.75 (quin, J=7 Hz, —$CH_2CH_2NH_3Cl$) 1.29 (broad, $(CH_2CH_2)_n$), 0.86 (t, J=7 Hz, —$CH_2$—$CH_3$).

Example 8

Preparation of the Polyolefin Z-A-$(CH_2)_3$—B (with Z=H; A=$(CH_2—CH_2)_n$, and B=$NH_2$)

6.3 ml (2.52 mmol) of $MgR_2$ prepared according to Example 6 (0.40 M in dibutyl ether) are introduced into a round-bottomed flask containing 400 ml of dry toluene.

The solution is transferred, under argon atmosphere, into a 500 ml reactor.

Next, a solution of 10.7 mg of compound $(C_5Me_5)_2NdCl_2Li.(OEt_2)_2$ (16 µmol) is transferred.

The argon is then eliminated under vacuum and the reactor is pressurized to 3 bar of ethylene at 70° C. The pressure in the reactor is kept constant during the polymerization by means of a tank.

When the desired amount of ethylene has been consumed, the reactor is degassed and the temperature is brought to 20° C.

A solution of methanol/HCl is added and the medium is stirred for 1 hour.

The resulting suspension is poured into a 1 M methanol/NaOH solution and stirred for 1 hour. The polymer is then filtered, washed with methanol, then dried.

5.0 g of polyethylene $CH_3$—$(CH_2CH_2)_n$—$(CH_2)_3NH_2$ are recovered (functionality 84%, Mn=1440 g·mol$^{-1}$ by NMR).

$^1$H NMR (2/1 v/v TCE/$C_6D_6$, 400 MHz, 363 K) dppm=2.53 (broad, $CH_2$—$NH_2$), 1.24 (broad, $(CH_2CH_2)_n$), 0.83 (t, J=7 Hz, —$CH_2$—$CH_3$).

Example 9

Preparation of the Polyolefin Z-A-$(CH_2)_3$—B (with Z=OH; A=$(CH_2—CH_2)_n$, and B=$NH_3Cl$)

6.3 ml (2.52 mmol) of $MgR_2$ prepared according to Example 6 (0.40 M in dibutyl ether) are introduced into a round-bottomed flask containing 400 ml of dry toluene.

The solution is transferred, under argon atmosphere, into a 500 ml reactor.

Next, a solution of 10.7 mg of compound $(C_5Me_5)_2NdCl_2Li.(OEt_2)_2$ (16 µmol) is transferred.

The argon is then eliminated under vacuum and the reactor is pressurized to 3 bar of ethylene at 70° C. The pressure in the reactor is kept constant during the polymerization by means of a tank.

When the desired amount of ethylene has been consumed, the reactor is degassed and a solution of triethyl borate $B(OEt)_3$ (2.55 ml in 10 ml of toluene, B/Mg=6) is added under argon. The medium is stirred for 2 h, then a solution of trimethylamine N-oxide TAO (2.5 g in 20 ml of DMF, TAO/B=1.5) is added under argon.

The medium is stirred for 2 h then the temperature is brought to 20° C.

A solution of methanol/HCl is added and the medium is stirred for 1 hour.

The polymer is then filtered, washed with methanol, then dried.

6.3 g of polyethylene HO—$CH_2$—$(CH_2CH_2)_n$—$(CH_2)_3NH_3Cl$ are recovered (functionality 70%, Mn=1940 g·mol$^{-1}$ by NMR).

$^1$H NMR (2/1 v/v TCE/$C_6D_6$, 400 MHz, 363 K) d ppm=8.63 (broad, —$NH_3Cl$), 3.40 (t, J=7 Hz, HO—$CH_2$—) 2.86 (broad, —$CH_2$—$NH_3Cl$), 1.75 (quin, J=7 Hz, —$CH_2CH_2NH_3Cl$) 1.29 (broad, $(CH_2CH_2)_n$).

Example 10

Preparation of the Polyolefin Z-A-$(CH_2)_3$—B (with Z=S—(C=S)—N$(CH_2—CH_3)_2$; A=$(CH_2—CH_2)_n$, and B=$NH_3Cl$)

6.3 ml (2.52 mmol) of $MgR_2$ prepared according to Example 6 (0.40 M in dibutyl ether) are introduced into a round-bottomed flask containing 400 ml of dry toluene.

The solution is transferred, under argon atmosphere, into a 500 ml reactor.

Next, a solution of 10.7 mg of compound $(C_5Me_5)_2NdCl_2Li.(OEt_2)_2$ (16 µmol) is transferred.

The argon is then eliminated under vacuum and the reactor is pressurized to 3 bar of ethylene at 70° C. The pressure in the reactor is kept constant during the polymerization by means of a tank.

When the desired amount of ethylene has been consumed, the reactor is degassed and a solution of tetraethylthiuram disulphide (1.5 g, 2 equivalents in 20 ml of toluene) is added under argon.

The medium is stirred for 2 h then the temperature is brought to 20° C.

A solution of methanol/HCl is added and the medium is stirred for 1 hour.

The polymer is then filtered, washed with methanol, then dried.

5.6 g of polyethylene $(CH_3—CH_2)_2N—(S=C)—S—CH_2—(CH_2CH_2)_n—(CH_2)_3NH_3Cl$ are recovered (functionality 100%, Mn=1480 g·mol$^{-1}$ by NMR).

$^1$H NMR (2/1 v/v TCE/C$_6$D$_6$, 400 MHz, 363 K) d ppm=8.59 (broad, —NH$_3$Cl), 3.64 (q, J=7 Hz (CH$_3$—CH$_2$)$_2$N—(S=C)—S), 3.30 (t, J=7 Hz, (CH$_3$—CH$_2$)$_2$N—(S=C)—S—CH$_2$—) 2.88 (broad, —CH$_2$—NH$_3$Cl), 1.77 (broad, —CH$_2$CH$_2$NH$_3$Cl), 1.67 (quin, J=7 Hz, (CH$_3$—CH$_2$)$_2$N—(S=C)—S—CH$_2$—CH$_2$—), 1.29 (broad, (CH$_2$CH$_2$)$_n$), 1.04 (t, J=7 Hz (CH$_3$—CH$_2$)$_2$N—(S=C)—S).

Example 11

Preparation of the Telechelic Polyolefin Z-A-(CH$_2$)$_3$—B (with Z=I; A=(CH$_2$—CH$_2$)$_n$, and B=NH$_3$Cl)

6.3 ml (2.52 mmol) of MgR$_2$ prepared according to Example 6 (0.40 M in dibutyl ether) are introduced into a round-bottomed flask containing 400 ml of dry toluene.

The solution is transferred, under argon atmosphere, into a 500 ml reactor.

Next, a solution of 10.7 mg of compound (C$_5$Me$_5$)$_2$NdCl$_2$Li.(OEt$_2$)$_2$ (16 µmol) is transferred.

The argon is then eliminated under vacuum and the reactor is pressurized to 3 bar of ethylene at 70° C. The pressure in the reactor is kept constant during the polymerization by means of a tank.

When the desired amount of ethylene has been consumed, the reactor is degassed and the temperature is brought to 20° C.

A solution of 2.5 g of iodine in THF (I/Mg mole ratio=4) is added and the medium is stirred for 2 hours.

A solution of methanol/HCl is added and the medium is stirred for 1 hour.

The resultant suspension is poured into methanol, then the polymer is filtered, washed in methanol, then dried.

6.3 g of telechelic polyethylene I—(CH$_2$CH$_2$)$_n$—(CH$_2$)$_3$NH$_3$Cl are recovered (functionality 100%, Mn=1300 g·mol$^{-1}$ by NMR).

$^1$H NMR (2/1 v/v TCE/C$_6$D$_6$, 400 MHz, 363 K) d ppm=8.30 (broad, —NH$_3$Cl), 2.91 (t, J=7 Hz, —CH$_2$I), 2.86 (t, J=7 Hz, —CH$_2$—NH$_3$Cl), 1.73 (quin, J=7 Hz, —CH$_2$CH$_2$NH$_3$Cl), 1.63 (quin, J=7 Hz, —CH$_2$CH$_2$I), 1.26 (broad, (CH$_2$CH$_2$)$_n$).

The invention claimed is:

1. A compound of formula (II) Y((CH$_2$)$_p$—B')$_m$, in which:
m=2;
Y is Mg;
B' is N(SiMe$_3$)$_2$ or N(SiMe$_2$CH$_2$CH$_2$SiMe$_2$); and
p is an integer from 1 to 50.

2. A compound according to claim 1, wherein p is an integer from 1 to 11.

3. A compound according to claim 1, wherein the compound corresponds to the formula Mg[(CH$_2$)$_p$—N(SiMe$_2$CH$_2$CH$_2$SiMe$_2$)]$_2$, with p=1 to 11.

4. A compound according to claim 1, wherein the compound corresponds to the formula Mg[(CH$_2$)$_p$—N(SiMe$_3$)$_2$]$_2$, with p=1 to 11.

5. A compound according to claim 1, wherein B' is N(SiMe$_2$CH$_2$CH$_2$SiMe$_2$).

6. A compound according to claim 1, wherein B' is N(SiMe$_3$)$_2$.

7. A compound according to claim 1, wherein the compound corresponds to the formula Mg[(CH$_2$)$_p$—N(SiMe$_2$CH$_2$CH$_2$SiMe$_2$)]$_2$, with p=3.

8. A compound according to claim 1, wherein the compound corresponds to the formula Mg[(CH$_2$)$_p$—N(SiMe$_3$)$_2$]$_2$, with p=3.

9. A method for synthesis of the compound of formula (II) Y((CH$_2$)$_p$—B')$_m$, comprising the reaction of the metal Y with a compound of formula X—(CH$_2$)$_p$—B';
X being a halogen;
m=2;
Y =Mg;
B' being selected from the group comprising N(SiMe$_3$)$_2$; N(SiMe$_2$CH$_2$CH$_2$SiMe$_2$); C$_6$F$_5$; C$_3$F$_7$; C$_6$F$_{13}$; para-C$_6$H$_4$ NMe$_2$; para-C$_6$H$_4$ O-Me; para-C$_6$H$_4$—N(SiMe$_3$)$_2$; and CH(OCH$_2$CH$_2$O); and
p being an integer from 1 to 50.

10. A method according to claim 9, wherein X is a bromine atom.

* * * * *